United States Patent [19]
Wikfors et al.

[11] Patent Number: 5,905,192
[45] Date of Patent: May 18, 1999

[54] METHOD FOR IDENTIFICATION OF CHROMATOGRAPHIC PEAKS

[75] Inventors: Edwin E. Wikfors, Landenberg, Pa.; Charles N. Carter, Newark, Del.

[73] Assignee: Hewlett-Packard Company, Palo Alto, Calif.

[21] Appl. No.: 08/899,420

[22] Filed: Jul. 23, 1997

[51] Int. Cl.$^6$ .......................... G01N 30/02; B01D 61/00; G06G 7/58
[52] U.S. Cl. .......................... 73/23.35; 364/498; 210/656
[58] Field of Search ................ 73/23.35, 23.36, 73/23.23; 364/498; 210/656

[56] References Cited

U.S. PATENT DOCUMENTS

| | | | |
|---|---|---|---|
| 3,898,837 | 8/1975 | Boege | 73/23.1 |
| 4,468,742 | 8/1984 | Jenden et al. | 364/497 |
| 4,802,102 | 1/1989 | Lacey | 73/23.1 |
| 4,941,101 | 7/1990 | Crilly . | |
| 5,119,315 | 6/1992 | Kemp et al. | 364/498 |
| 5,121,443 | 6/1992 | Tomlinson | 73/23.23 X |
| 5,347,475 | 9/1994 | Taylor et al. | 364/571.01 |
| 5,436,166 | 7/1995 | Ito et al. | 73/23.36 X |
| 5,670,379 | 9/1997 | Ito et al. | 73/23.36 X |
| 5,699,270 | 12/1997 | Ashe et al. | 364/500 |

OTHER PUBLICATIONS

Brochure, entitled "Microbial Identification System"; MIDI, Newark, DE; Feb. 1989.
User's Manual, "Microbial IdentificationSystem—Library Generation Software"; Original Printing Apr., 1988.

*Primary Examiner*—Hezron Williams
*Assistant Examiner*—Jay L. Politzer
*Attorney, Agent, or Firm*—Mark Z. Dudley

[57] ABSTRACT

Method and apparatus are provided for peak identification of sample peaks in a chromatogram, wherein at least one group of standard peaks in standard peak series is matched to at least one group of sample peaks in a sample peak series so as to perform proper identification of the sample peaks in the sample peak group. In a preferred method, a succession of retention time windows are determined according to the characteristic retention times of the standard peaks and according to steps for determining shift, stretch, and distort parameters. The retention time windows are located with respect to the sample peak series and in accordance with the shift, stretch, and distort parameters so as to capture only certain ones of the sample peaks in the sample peak series. The shift, stretch, and distort parameters are used to position the retention time windows for improved matching of the standard peaks in the standard peak group to the captured sample peaks.

13 Claims, 9 Drawing Sheets

METHOD FOR IDENTIFICATION OF CHROMATOGRAPHIC PEAKS

FIELD OF THE INVENTION

The present invention relates to chromatographic analysis systems and, more particularly, to a method and apparatus for analyzing a sample comprised of several components to determine the identity and concentration of each component in the sample. More specifically, this invention is related to a method of analyzing data provided by a detector in a chromatographic apparatus to determine the composition of a sample.

BACKGROUND OF THE INVENTION

Chromatography is a known method of analyzing a sample comprised of several components to qualitatively determine the identity of the sample components as well as quantitatively determine the concentration of the components.

A typical gas chromatographic apparatus includes an injection port into which the sample is injected and mixed with an inert gas at high temperature, a column through which the various dissolved components of the sample will travel at a rate related to the characteristics of the specific components, and a detector for measuring the retention time of each component. The time between the injection of a sample and the detection of a specific component is called the retention time for that component. The results of a chromatographic separation are displayed as a plot of detector signal versus time, commonly known in the art as a chromatogram. A chromatogram typically comprises a plurality of peaks wherein each peak corresponds to a certain component of the analyzed sample. The area of the peak is to some degree characteristic of the amount of the respective component present in the sample. In order to insure a reliable qualitative and quantitative analysis of the sample, it is necessary that the chromatograph perform proper identification of those peaks in the chromatogram that represent certain compounds present in the sample.

As various components will have different retention times, the chromatogram will usually provide a series of Gaussian-shaped sample peaks wherein each peak represents a respective component in the sample. Ideally, a chromatogram of a sample containing, e.g., a plurality of components, should have a respective plurality of clearly separate and identifiable peaks. Such a chromatogram may thus be analyzed to determine the identity of the respective components by noting the time occurrence of each sample peak and comparing the observed retention time of a sample peak in the chromatogram to a characteristic retention time for a known, or standard, peak that is derived from a standard mixture of known components. Since the retention time is a unique physical characteristic of each different component, the observed retention time at which each sample peak occurs may be compared to the characteristic retention times of compounds in a standard mixture so as to allow one to assign, or name, an identity to each component in the sample under investigation.

Retention time is typically considered to be a function of the flow rate of the fluid, which in turn is a function of operating parameters such as the column dimensions or temperature, the inlet outlet pressure, and the gas viscosity. Because the retention time of a component is subject to variations in the operating parameters, retention time stability in a chromatographic system is a desirable characteristic that determines the ability of the system to properly identify closely eluting components and to allow a component to be identified within a desired identification window of time. However, retention time stability is not often achieved without use of extensive methods and apparatus for calibration. Conventional analytical methods have heretofore included techniques such as frequent recalibration so as to correct for any systematic errors or shift due to instability in the retention time.

Some conventional chromatographic equipment incorporate a form of a peak identification algorithm for improving the process of assigning compound names to the observed chromatographic peaks based on the observed retention times. These algorithms are based upon the use of a fixed retention time window for identification of a given peak. The conventional algorithm may be understood as follows. If the observed retention time of a given peak in a sample falls within a window centered on a characteristic retention time known to be associated with a compound, the respective compound name is assigned to that peak. If a plurality of peaks occur within the window, the peak nearest the known retention time for the compound is assigned the compound name.

The window size is sometimes determined as a percentage of the characteristic retention time for the given compound. However, because the retention times of components will change, a wide retention time window is often selected to capture and thus locate a given peak of interest. This step also requires intervention by the user, e.g., by editing the characteristic retention time for a given compound. Further, as the retention time window becomes larger, unwanted peaks are captured by the window and accordingly it is difficult to resolve which of the peaks within a window is the peak of interest. If the window is made too small, the system may not be able to recalibrate; and the performance of the system is then subject to drift. Some complex algorithms have been employed that track and adjust for drift between calibrations; however, this approach is nonetheless disadvantageous because each copy of an chromatographic method may be the result of a different data reduction method and the characteristic retention time for a given compound will vary according to the instrumentation used to determine the characteristic retention time. Also, the data reduction method will change when a column is replaced or reduced in length.

An improved approach was used in a microbial identification system commercially available in the Hewlett-Packard Model HP5898A Chromatograph, wherein peaks were located in an analysis of a calibration sample in a calibration sequence so that the retention times of the calibration sample peaks could be used to determine a calibration table of retention time indices. The retention time indices were then used in performing peak identification. The peak location algorithm employed an algorithm that included move, stretch, and distort parameters for improved peak location in the presence of spurious peaks due to noise and other artifacts. However, the peak location algorithm typically required that each and every peak of interest in the calibration sample be identified for the algorithm to succeed. If not, the algorithm would fail and a failure mode would be declared.

Several shortcomings remain in the above-described approaches. Firstly, it is undesirable to require that all peaks in a chromatogram must be identified for a peak identification method to succeed. Secondly, the aforementioned approaches are not amenable to the identification of groups of peaks that may have been recorded in a chromatogram generated by the use of multiple columns or according to techniques known in the art as heart cutting or multidimensional chromatography.

SUMMARY OF THE INVENTION

According to the present invention, a method is provided for peak identification of sample peaks in a chromatogram, wherein a group of standard peaks in a standard peak series is sequentially matched to certain sample peaks in a sample peak series so as to perform proper identification of the sample peaks.

In the preferred method, a series of retention time windows are created in accordance with the standard peaks. Each retention time window is determined according to the location of its respective standard peak and according to steps for determining one or more shift, stretch, and distort parameters. One or more of the shift, stretch, and distort parameters are used to position each retention time window. The series of retention time windows is thereby applied to the sample peak series and in accordance with the shift, stretch, and distort parameters so as to capture only a minimal number of the sample peaks in each retention time window. As a result, there is improved matching of the standard peak to the captured sample peak(s) in the sample peak group.

In one aspect of the preferred method, the retention time windows are applied in a fashion such that each standard peak is compared to each of the sample peak(s) captured in a given window so as to determine one or more matched pairs of peaks. That is, for each peak in the standard peak group that corresponds to a certain one of the peaks in the sample peak series, a matched pair is determined. Preferably, at least three matched pairs are determined for the matching to be consider valid.

In another aspect of the preferred method, the retention time windows are applied in a fashion such that in the event that a plurality of sample peaks are captured in a given retention time window, each of the captured sample peaks is considered as a candidate sample peak, and a plurality of matched pairs are then determined from a given standard peak. A quality factor representing the correspondence of the standard peak to each of the candidate sample peaks in the matched pairs is determined. The resulting quality factors may be compared to determine a best match of the standard peak to one of the candidate sample peaks. The candidate sample peak in the best matched pair is then identified with the compound associated with the respective standard peak.

In another aspect of the preferred method, it is contemplated that there may be an instance wherein a retention time window does not captures any sample peak. In such an instance, the sample peak is simply assumed to be missing, the particular retention time window is removed, and the standard peak with which it is associated is overlooked. The next, i.e., (I+1)th, retention time window is created in the same fashion as the prior retention time window but at the next expected retention time, i.e., at $t_{X(n+1)}$, and the corresponding sample peak thus captured is associated with the next, i.e., (I+1)th, standard peak. In any instance wherein a sample peak is assumed to be missing, the particular retention time window is removed, a succeeding retention time window is created, and so on, until a sample peak is captured or until the use of the standard peak group is exhausted. In the latter event, the method may then proceed with matching another.

In another aspect of the preferred method, the retention time windows are applied in a fashion such that first, second, . . . ith standard peaks are sequentially selected from a standard peak group and compared to a series of sample peaks, so as to match at least n standard peaks to n sample peaks, wherein n preferably equals 3 or more. For example, a first standard peak is selected; a first sample peak in a sample peak series is then located and captured by placing a first window on the chromatogram at a first expected retention time $t_{X1}$ wherein the first expected retention time $t_{X1}$ is determined from a first characteristic retention time $t_1$ associated with the first standard peak. At least one first sample peak is captured in the first retention time window. The difference between the observed retention time $t_A$ of the first sample peak and the first characteristic retention time $t_1$ allows a determination of a shift parameter S. (If plural sample peaks are captured in the first retention time window, each of these sample peaks are considered a candidate sample peak and the observed retention time of each candidate sample peak is used in the determination of a respective shift parameter S', S", etc.) A second sample peak in the sample peak series is then located by placing a second retention time window on the chromatogram at a respective expected retention time $t_{X2}$ wherein the second expected retention time $t_{X2}$ is determined from a second characteristic retention time $t_2$ associated with the second standard peak. However, the second expected retention time $t_{X2}$ also includes a time shift according to the shift parameter S. At least a second sample peak is located and captured in the second retention time window. A stretch parameter R is then determined according to the ratio of: a) the difference between an observed retention time $t_B$ of the second sample peak and an observed retention time $t_A$ of the first sample peak, and b) the difference between the characteristic retention time $t_2$ of the second standard peak and the characteristic retention time $t_1$ of the first standard peak. (If plural sample peaks are captured in the second retention time window, each of these sample peaks is considered a candidate sample peak and the observed retention time of each candidate sample peak is used in the determination of respective stretch parameters R', R", etc.) A third sample peak in the sample peak series is then identified by placing a third retention time window on the chromatogram at a respective expected retention time $t_{X3}$. The respective expected retention time $t_{X3}$ is determined from a third characteristic retention time $t_3$ associated with the third standard peak as provided by the formula: $t_{X3}=t_B+R(t_3-t_2)$. At least one third sample peak is located and captured in the third retention time window. A distort parameter $D_1$ is then determined as the difference between the observed retention time $t_C$ of the third candidate peak and the expected retention time $t_{X3}$. (If plural sample peaks are captured in the third retention time window, each of these sample peaks is considered a candidate sample peak and the observed retention time of each candidate target is used in the determination of a respective distort parameter D', D", etc.) The foregoing step for determination of a distort term $D_1$ may be repeated to provide successive retention time windows at fourth, fifth, . . . ith expected retention times to capture respective fourth, fifth,. . . ith sample peaks, as may be provided according to the formula:

$$t_{ei}=t_{(I-1)}+R(t_i-t_{(I-1)})$$

Similarly, additional respective distort terms $D_2$, $D_3$, $D_4$, . . . etc. may be determined as well.

The sample peak thus captured in the respective retention time window provide an opportunity to match the sample peak to the respective standard peak. Each sample peak that is captured in its respective retention time window can be considered to be paired with the respective standard peak that was used to generate the retention time window. For example, the first sample peak that is located in the first retention time window will be identified as being paired with to the first standard peak, to generate a first pair, and so on. If there is only one pair determined for a given retention time window, then the sample peak in that pair is matched with the standard peak. The pair is then considered to be "matched" and the sample peak is named according to the compound name known to be associated with its respective standard peak.

As mentioned above, if more than one sample peak is captured in a retention time window, each of such sample peaks is considered to be a candidate sample peak in a candidate sample peak set. Each candidate sample peak in the set is used to calculate a respective shift, stretch, or distort parameter, depending upon the location of the particular retention time window. Upon the determination of a plurality of such parameters, a next, i.e., (I+1)th, retention time window is created for capturing the next (I+1)th sample peak. If plural candidate sample peaks are then captured, that set is related to the respective standard peak, to provide a respective candidate sample peak set. For example, if a plurality of candidate sample peaks are discerned in the first retention time window, a plurality of shift parameters are determined (S, S', S", . . . etc.) from the respective plurality of candidate sample peaks. The first of these shift parameters (S) is then used to locate a second retention time window so as to capture any peaks set that may be paired with the second standard peak. Each of the sample peaks captured in the second retention time window are then used as candidate sample peaks for determining a series of respective stretch parameters (R, R', R", . . . etc.) In turn, each of these stretch parameters (R, R', R", . . . etc.) is then used to locate respective third retention time windows so as to capture any peaks in the sample peak series that may be paired with the third standard peak. As the method proceeds in a recursive fashion, a plurality of peak pair sets are generated until all possible pairs of the captured sample peaks and their respective standard peaks are made. For each set, a resulting string of error terms in an error term series $e_1, e_2, e_3, \ldots e_n$ may be determined to provide a respective quality factor. For example, in an instance wherein: the first retention time window captures three peaks, the second retention time window captured two peaks, and the remaining third and fourth retention time windows each captured one peak, the plurality of peak pair sets would render the following error term sums . . .

$Q_1$=First Sum=$(S)^2+(R)^2+(D_1)^2+(D_2)^2$
$Q_2$=Second Sum=$(S)^2+(R')^2+(D_1)^2+(D_2)^2$
$Q_3$=Third Sum=$(S')^2+(R)^2+(D_1)^2+(D_2)^2$
$Q_4$=Fourth Sum=$(S')^2+(R')^2+(D_1)^2+(D_2)^2$
$Q_5$=Fifth Sum=$(S")^2+(R)^2+(D_1)^2+(D_2)^2$
$Q_6$=Sixth Sum=$(S")^2+(R')^2+(D_1)^2+(D_2)^2$ A best match determination may then be applied to each of the quality factors.

Alternatively, the quality factor may be determined according to a first criterion associated with the number of captured peaks in the set, and a second criterion associated with the minimum sum of the squares of the error terms in the error term series devoted to the set. The quality factors may be compared and the best quality factor indicates that its respective set is a best match.

In another alternative, the quality factors for two sets may be determined and compared to determine a current best match, whereupon successive quality factors in successive sets may be compared to the current best match.

In still another alternative, the quality factors for the entire plurality of the sets may be determined and collectively compared to determine a single best match among the plurality.

In another aspect of the preferred method, each retention time window may be determined to exhibit a width that is predetermined, or subject to a user-inputted variable, or variable depending upon the numbering of the retention time window. For example, the first, second, . . . etc. retention time windows may be determined to have decreasing widths as the windows increase in number.

In another aspect of the method, peak identification is provided wherein each peak in a standard peak group may be tagged with a component name, a characteristic retention time, and a group identifier, such that the peak pattern set is more useful in the identification of the peaks in a sample peak set that comprises groups of sample peaks.

In another aspect of the method, peak identification may be provided wherein each peak in a standard peak group is optionally be required to be matched with at least one sample peak. In the event this condition is not met, the match may be considered invalid.

In another aspect of the method, peak identification may be provided wherein each sample peak in a matched pair is optionally be required to exhibit a certain area percentage value. In the event this condition is not met, the match may be considered invalid.

ADVANTAGES OF THE INVENTION

In a feature of the contemplated method, peak identification is successfully accomplished for a group of sample peaks in a sample peak series even though a particular standard peak is not matched to any sample peak present in the sample peak series; for example, the method is successful even though the number of sample peaks in the sample peak group may be less than the number of peaks in the standard peak group.

In another feature of the method, peak identification is provided wherein plural groups of sample peaks within a sample peak series may be independently correlated to groups of standard peaks via the use of unique shift, stretch, and distort parameters that are applicable to each of the groups of sample peaks. Such capability allows the method to be applied to a sample peak series which comprises groups of sample peaks wherein the groups have been generated by respectively differing columns operated, e.g., in a multidimensional chromatographic analysis.

In another feature of the method, peak identification is provided in a chromatographic system even though the retention time stability of the system may be sub-optimal or degraded. Retention time stability therefore need not be maintained to a stringent level, and thus the preferred method is especially suited for operation in chromatographs that exhibit less than optimal retention time stability. For example, in comparison to advanced chromatographs, the preferred method may be advantageously employed in older, simpler, or less-expensive chromatographs, or in chromatographs that do not benefit from frequent maintenance or extensive calibration.

In another feature of the method, reliable peak identification is provided in a chromatographic system that performs an analytical method even though the chromatographic system is subject to variations (i.e., "drift") in its operating conditions, parameters, tolerances, etc.

In another feature of the method, reliable peak identification is provided in a chromatographic system that performs an analytical method even though the analytical method has been transported from one between chromatographic system to another.

In the drawings and in the following detailed description of the invention, like elements are identified with like reference numerals. Note that, for the purpose of clarity in illustration, FIGS. 3–8 include schematic illustrations of peaks of uniform height that are representative of a few component compounds; in actual practice, such peaks may vary in their height, quantity, and distribution.

DETAILED DESCRIPTION OF THE PREFERRED EMBODIMENTS

The method of the present invention may be employed to improve the detection of a variety of sample compounds present in a fluid in an analytical chromatographic system. Such fluid is intended to include gases, liquids, multiple component gases and liquids, and mixtures thereof capable of regulated flow. Gases are the preferred fluids according to the practice of the present invention, and therefore the following description of the invention will be directed to a gas chromatographic analytical system. However, it should be understood that the teachings herein are applicable to chromatographic analysis of gases, liquids, and other compressible fluids.

In analytical chemistry, liquid chromatography (LC) and gas chromatography (GC) techniques have become important tools in the identification of chemical sample components. The basic mechanism underlying chromatographic analysis is the separation of a sample chemical mixture into individual components by transporting the mixture in a carrier fluid through a specially prepared separation column having a retentive media therein. The carrier fluid is referred to as the mobile phase and the retentive media is referred to as the stationary phase. The principal difference between liquid and gas chromatography is that the mobile phase is either a liquid or a gas, respectively. The analytical choice between liquid and gas chromatography techniques is largely dependent on the molecular weight of the components to be analyzed. Liquid chromatography devices are capable of analyzing much heavier compounds than gas chromatography devices. However, in some instances gas chromatography detection techniques are more sensitive and therefore may be preferred.

In a gas chromatographic analysis, an inert carrier gas is passed through a temperature-controlled column which contains a stationary phase in the form of porous sorptive media, or through a hollow capillary tube having an inner diameter in the range of few hundred microns coated with the stationary phase. A sample of the subject mixture is injected into the carrier gas stream and passed through the column. As the subject mixture passes through the column, it separates into its various components. Separation is due primarily to differences in the partial pressures of each sample component in the stationary phase versus the mobile phase. These differences are a function of the temperature within the column. A detector, positioned at the outlet end of the column, detects each of the separated components contained in the carrier fluid as they exit the column.

The term "detector" refers to a physiochemical data output means, and in particular to means for providing sample peak data representative of information useful as a chromatogram, and includes a wide variety of useful chromatographic detectors, such as the flame ionization detector (FID), photoionization detector (PID), nitrogen phosphorous detector (NPD), flame photometric detector (FPD), thermal conductivity detector (TCD), atomic emission detector (AED), electrolytic conductivity detector (ELCD), and electron capture detector (ECD). Mass spectral detectors and infrared spectral detectors are also known.

The terms "multidimensional chromatography" refers to a separation process in which a single sample is subjected to a sequence of chromatographic separations, each of which acts upon all or part of the separated components from a previous chromatographic step, and differs in its relative selectivity or capacity.

The terms "sample peak" refer to a peak which is present in a chromatogram and which represents at least one of a series of compounds in a sample, wherein the compound is initially unidentified.

The terms "standard peak" refer to a peak that is present in a chromatogram developed from a known series of compounds in an analytical method employed by a chromatograph of interest. The standard peak(s) thus represents a known series of compounds and thereby is employed according to the present invention as a standard for comparison with, and identification of, one or more sample peaks generated by a sample analysis that uses the same or equivalent analytical method.

The terms "sample peak series" refer to a series of sample peaks within which the sample peaks may be matched to standard peaks, and as a result, be grouped in at least one sample peak group.

The terms "standard peak series" refer to a series of standard peaks within which the standard peaks may be presented or, in some applications, grouped in at least one standard peak group.

The terms "sample peak group" refer to a plurality of sample peaks which have been matched or are being matched to respective standard peaks in a standard peak group. The contemplated matching is performed with use of one or more move, stretch, and distort parameters as are described herein.

The terms "standard peak group" refer to a plurality of standard peaks which have been matched or are being matched to respective sample peaks in a sample peak group. The contemplated matching is performed with use of one or more move, stretch, and distort parameters as are described herein.

The terms "characteristic retention time" refers to the retention time known for a particular standard peak in a standard peak group.

The terms "observed retention time" refer to the retention time observed for a particular sample peak in a sample peak group.

The terms "expected retention time" refer to a newly-calculated retention time that is derived from the characteristic retention time of a standard peak, but which is further adjusted by use of one or more shift, stretch, and distort parameters according to the peak identification method taught herein.

Figure 1A:
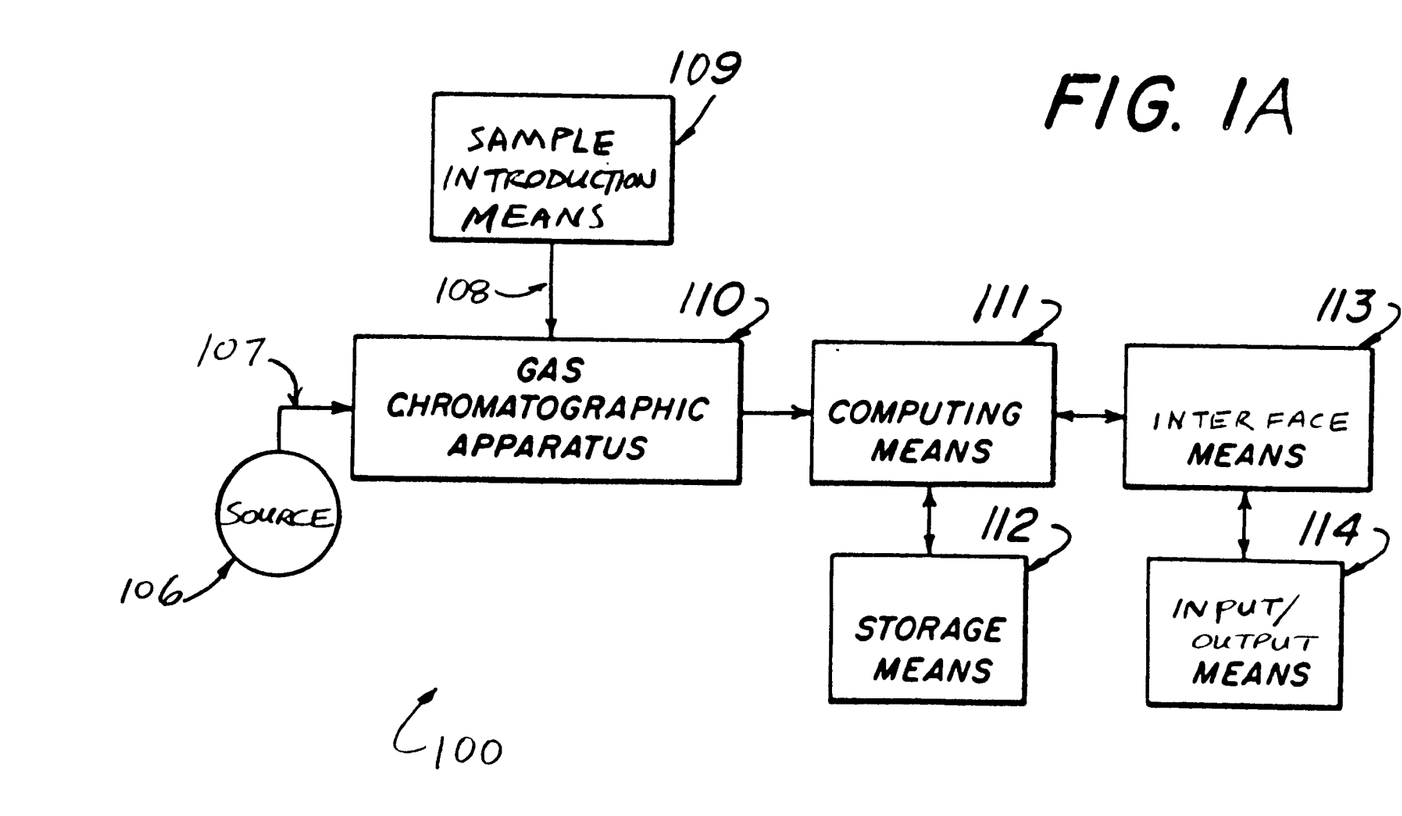
FIG. 1A is a block diagram of an analytical apparatus suitable for the practice of the present invention.
Figure 1B:
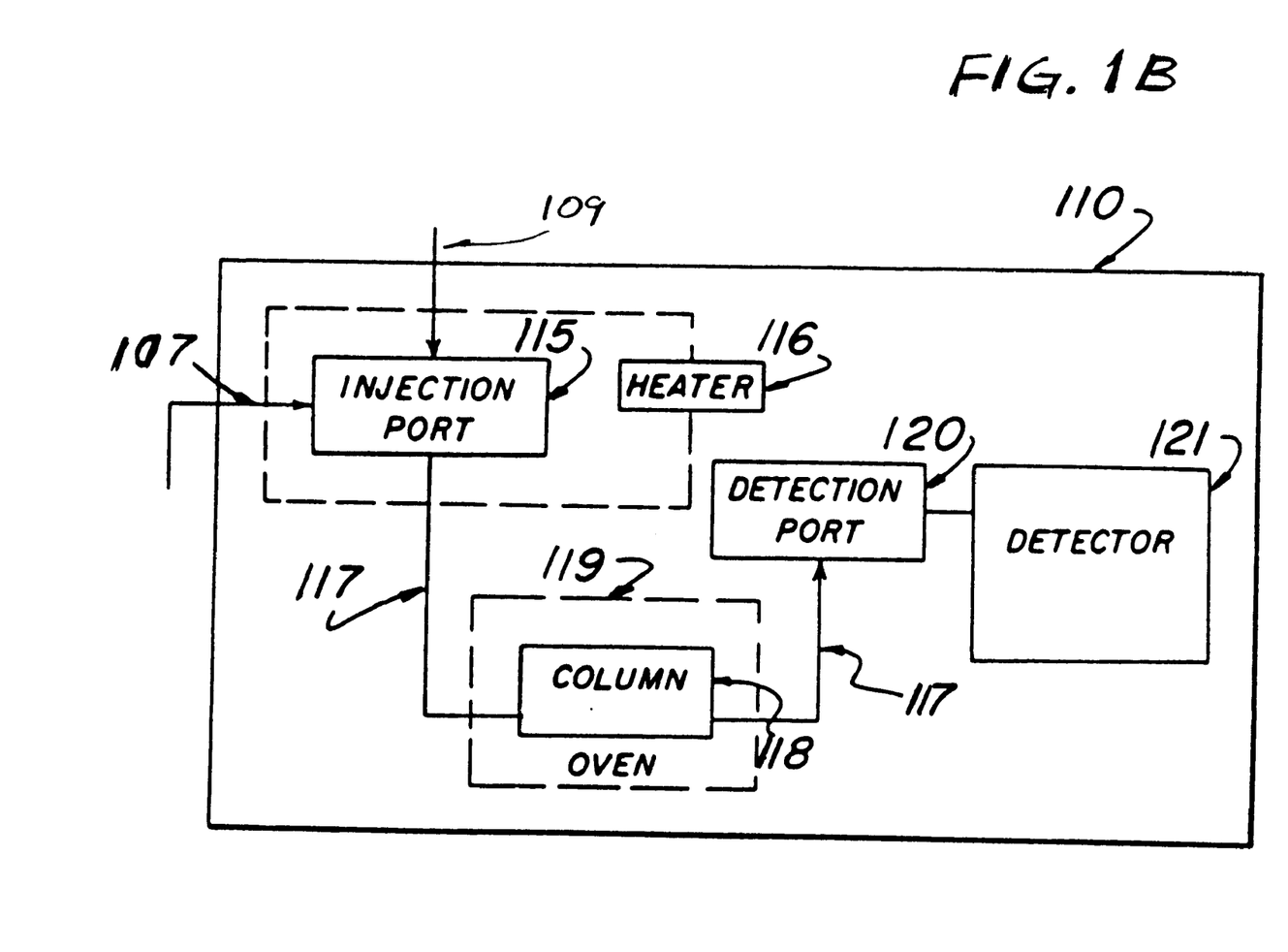
FIG. 1B is a block diagram of a typical gas chromatographic apparatus which may be utilized with the apparatus of FIG. 1.
Figure 2:
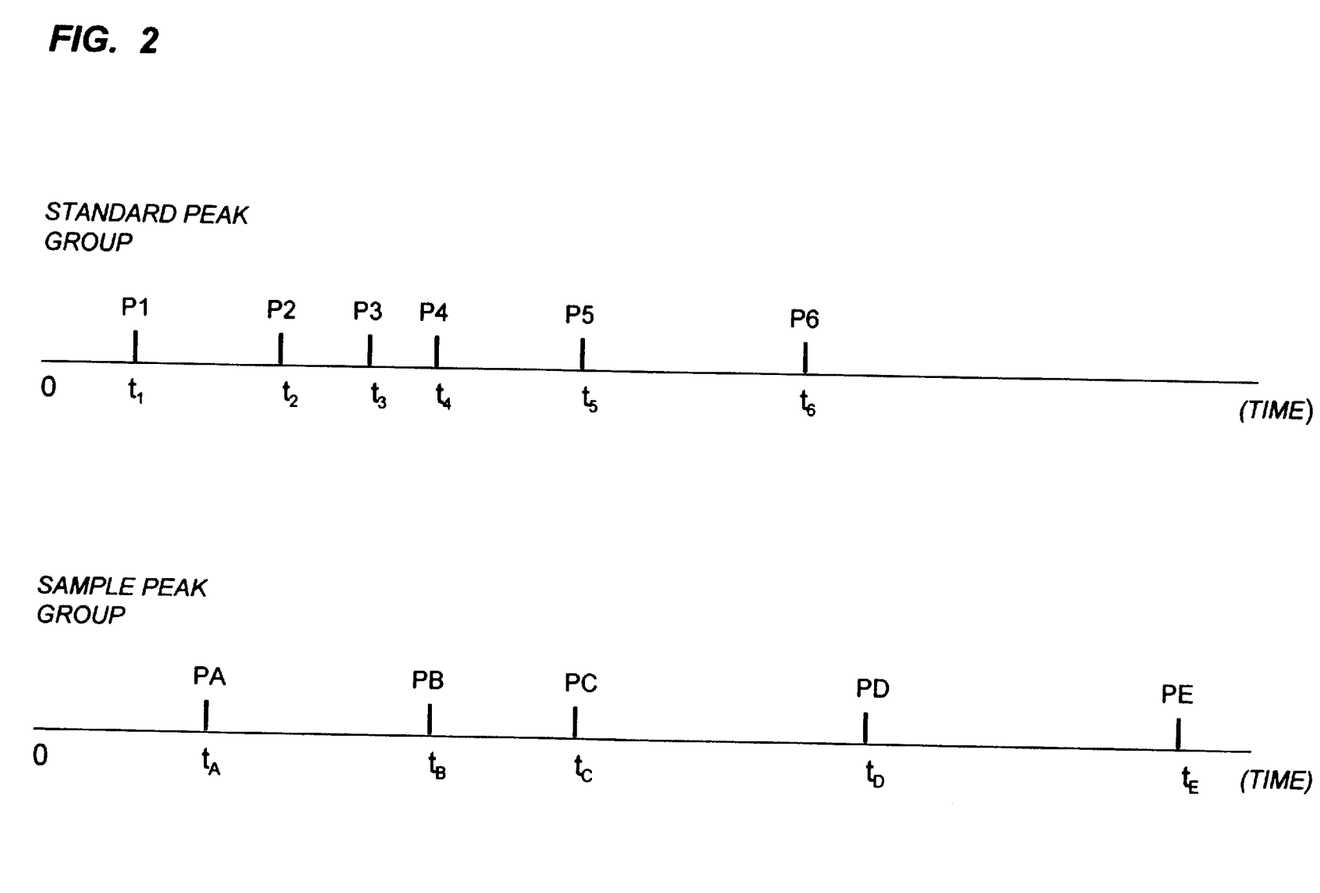
FIG. 2 is a simplified schematic representation of a standard peak group and a sample peak group used in an algorithm for identification of sample peaks in a sample peak series.

A preferred embodiment of an analytical instrument system 100 illustrated in FIGS. 1A, 1B includes a sample introduction means 109, a gas chromatographic apparatus 110, computing means 111, storage means 112, interface means 113, and input/output means 114. In order to perform a chromatographic separation of a sample, introduced on line 108, a quantity of the sample is injected into a fluid stream, preferably in the form of a pressurized carrier gas, by means of an injection port 115 that is supplied with carrier gas stream 117. The carrier gas is supplied on source line 107 to the injection port 115 from a source 106. The carrier gas may comprise one or more component gasses—such as, for example, hydrogen, nitrogen, or helium—depending upon the particular chromatographic separation to be performed.

The injection port 115 provides a portion of the sample/carrier gas mixture to a separation column 118. The column 118 is positioned within a temperature-controlled thermal chamber, or oven 119. The oven 119 preferably includes a heater 116. In order to ensure that the temperature within the oven 119 is at a desired level, the temperature in the oven 119 is provided to interface 113 and the processor 111. The heater 116 maintains a controlled temperature in the oven 119 in response to a control signal generated by the computing means 111. The carrier gas/sample combination passing through the column 118 is thereby exposed to a temperature profile resulting from the operation of the heater 116 within the oven 119. Typically, the temperature in the oven 119 is controlled according to a selected program so that the sample will separate into its components.

As the carrier gas (containing the sample) exits the column 118, the presence of one or more sample constituent components is detected by a detector 121. The detector 121 can be any of the GC detectors known in the art, so long as it is capable of determining at least one physicochemical property of the sample components which exit the column 118. The detector output signal is then received by the computing means 111 and optionally stored in the storage means 112. Preferably, the detector output signal is provided in the form of data representative of a series of sample peaks in at least one sample peak series. As will be described below, the sample peaks may be identified and presented in one or more sample peak series. Each sample peak series is analyzed with aid of a novel peak identification method based on data representative of one or more selected standard peak groups. Preferably, data representative of the standard peak group(s) has been predetermined or inputted at the input/output means 114 and stored in the storage means 112.

The computing means 111 may include computing devices amenable to the practice of this invention, e.g., one or more computing devices such computers, microprocessors, micro controllers, switches, logic gates, or any equivalent logic device capable of performing the computations described hereinbelow. Computing means 111 preferably is coupled with interface means 113 and information input/output means 114; the latter preferably includes a keyboard, keypad, or computer mouse, or remote processor (not shown) for inputting operating condition parameters, system data, and the like. Information input/output means 114 may include display means such as an alphanumeric or video display, a printer, or similar means. The preferred processor 111 may further include storage means 112 in the form of volatile and non-volatile memory devices in which input and output information, operating condition parameters, system information, and programs can be stored and retrieved. Operating commands, device and fluid type information, detector response attributes, column temperature programs, and other information necessary to perform a chromatographic analysis may be entered into the processor 111 by way of the input output means 114 or retrieved from storage means 112. Messages prompting the user to enter certain information, such as a desired operating parameter, can be generated by the processor 111 and displayed on the display. The interface means 113 may further comprise network and bus system (input/output or I/O) controllers, isolation devices, clocks, and other related electronic components for performing control, processing, and communication tasks other than those described herein.

Turning now to FIGS. 2–8, it will be understood that the system 100 may be operated according to a preferred embodiment of a peak identification method according to one or more programs operable in the computing means 111 for matching a standard peak group of standard peaks P1, P2, P3 . . . Pn (where, in the illustrated embodiment, n=6) in a standard peak series to a chromatogram that includes at least one sample peak group having sample peaks PA, PB, PC, PD, and PE.

Figure 3:
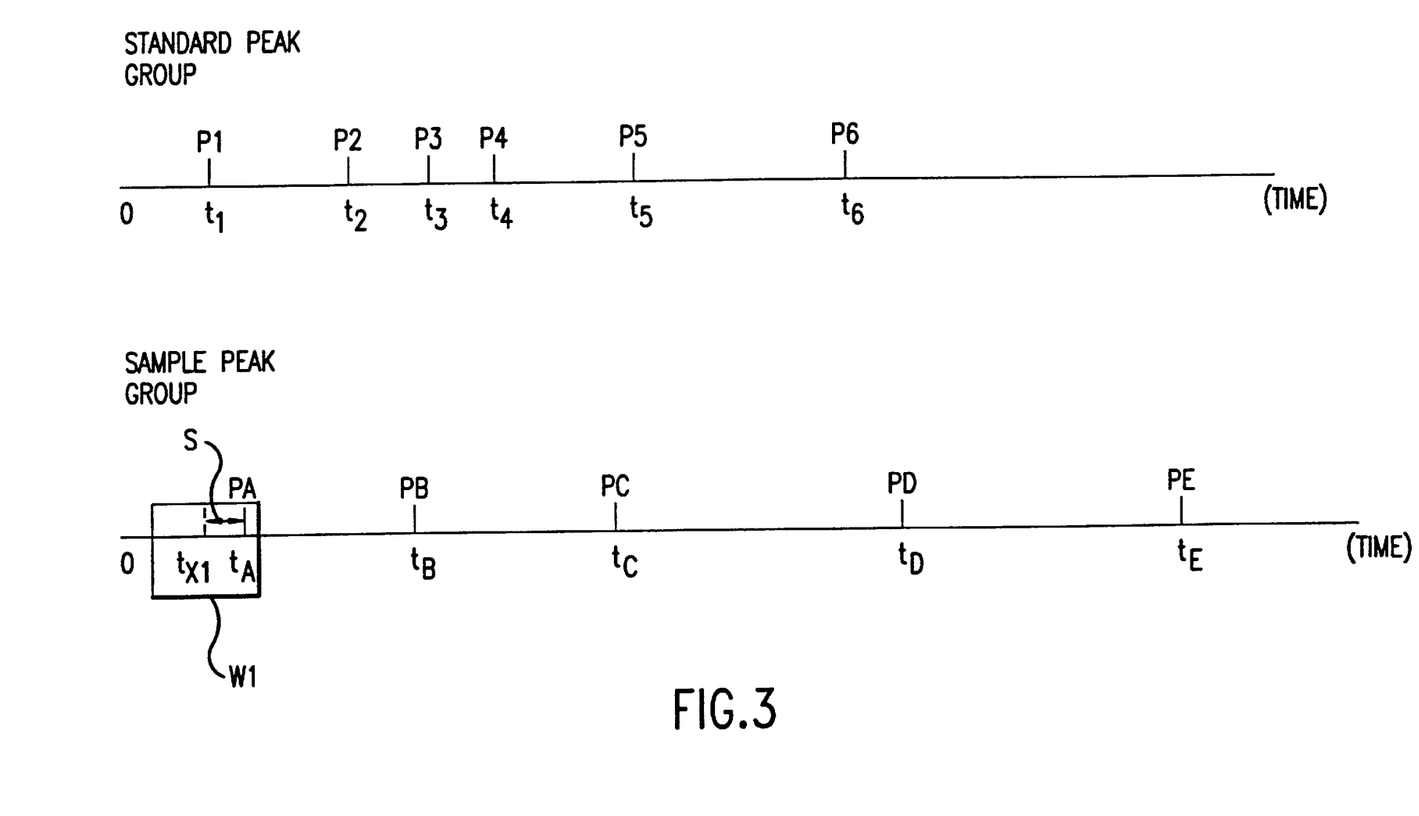
FIG. 3 is a simplified schematic representation of the standard peak group and the sample peak group of FIG. 2, illustrating a method step for determining a shift parameter.

The peak identification method begins with a first step illustrated in FIG. 3 in which a first standard peak P1 is selected and a first retention time window W1 is applied to the sample peak series at an expected retention time $t_{X1}$ derived from the characteristic retention time $t_1$ of the first standard peak P1. The size of this window W1 is predetermined or set by a user-defined input parameter. This first window W1 is generally of a size sufficient to correct for errors in certain operating conditions such as oven temperature and column flow rate which may have been the source in the shift in the elution time of the sample peak group. At least one sample peak, such as a sample peak PA, may then be captured within the window W1 and becomes a candidate for a match with the first standard peak P1. Accordingly, sample peak PA may potentially be matched with the first standard peak P1 and identified with the compound associated with the first standard peak P1.

In the first window W1, one sample peak is illustrated as being captured for clarity. If there were no sample peaks found within the first window W1, the algorithm would assume that the compound associated with the first standard peak P1 is absent in the sample. The peak identification method would then continue by removing the first retention time window W1 and applying another window to the sample peak group but at a time corresponding to the characteristic retention time of the next standard peak. For example, if the first window W1 failed to capture a sample peak, no sample peak would be considered to be matched with the standard peak P1 and the next standard peak to be used would be standard peak P2. The peak identification method would then continue by application of the window W2 to the sample peak group at a time corresponding to the characteristic retention time of standard peak P2. This progression is continued with successive peaks P3, P4, etc. until at least one sample peak is captured, or until the final peak is reached, whichever is earlier.

As illustrated in FIG. 3, the first retention time window W1 is shown to have captured one sample peak, i.e., sample peak PA. As there is only one peak found in the first window W1, the sample peak PA is then considered to be matched to the respective standard peak P1. A shift parameter S is determined from the captured sample peak. The shift parameter S is determined as the difference between the characteristic retention time of the pertinent standard peak and the retention time observed for the captured sample peak. As illustrated in FIG. 3 the shift parameter S is measured as:

$$S = t_{SAMPLE\ PEAK} - t_{CHARACTERISTIC} = t_A - t_1$$

The determination of a shift parameter S serves two purposes. Firstly, this shift parameter S is used in subsequent steps to determine: a stretch parameter R, one or more distort parameters $D_3, D_4, D_5, \ldots D_n$, and the proper placement of subsequent second, third, etc. retention time windows. Secondly, it can be used as described herein below as a first error term in an error term series that is useful in determining a quality factor or a best match condition for matching a standard peak group and sample peak group.

If more than one a sample peak is captured in the window W1, the method presumes each captured sample peak to be a candidate for a match with the respective standard peak, and will proceed in determining a series of shift parameters (S, S', S" . . . etc.) that are respectively derived from each candidate sample peak. That is, each candidate sample peak in the first window W1 results in a stretch parameter that is unique to the respective candidate sample peak. The process then continues recursively with the remaining peaks in the standard peak group. That is, each candidate sample peak in the first window WI is used to determine a particular shift parameter which is unique to that candidate peak. The method proceeds in the subsequent steps described below to match the standard peaks with the remaining sample peaks by using the particular candidate peak as a starting point.

Figure 4:
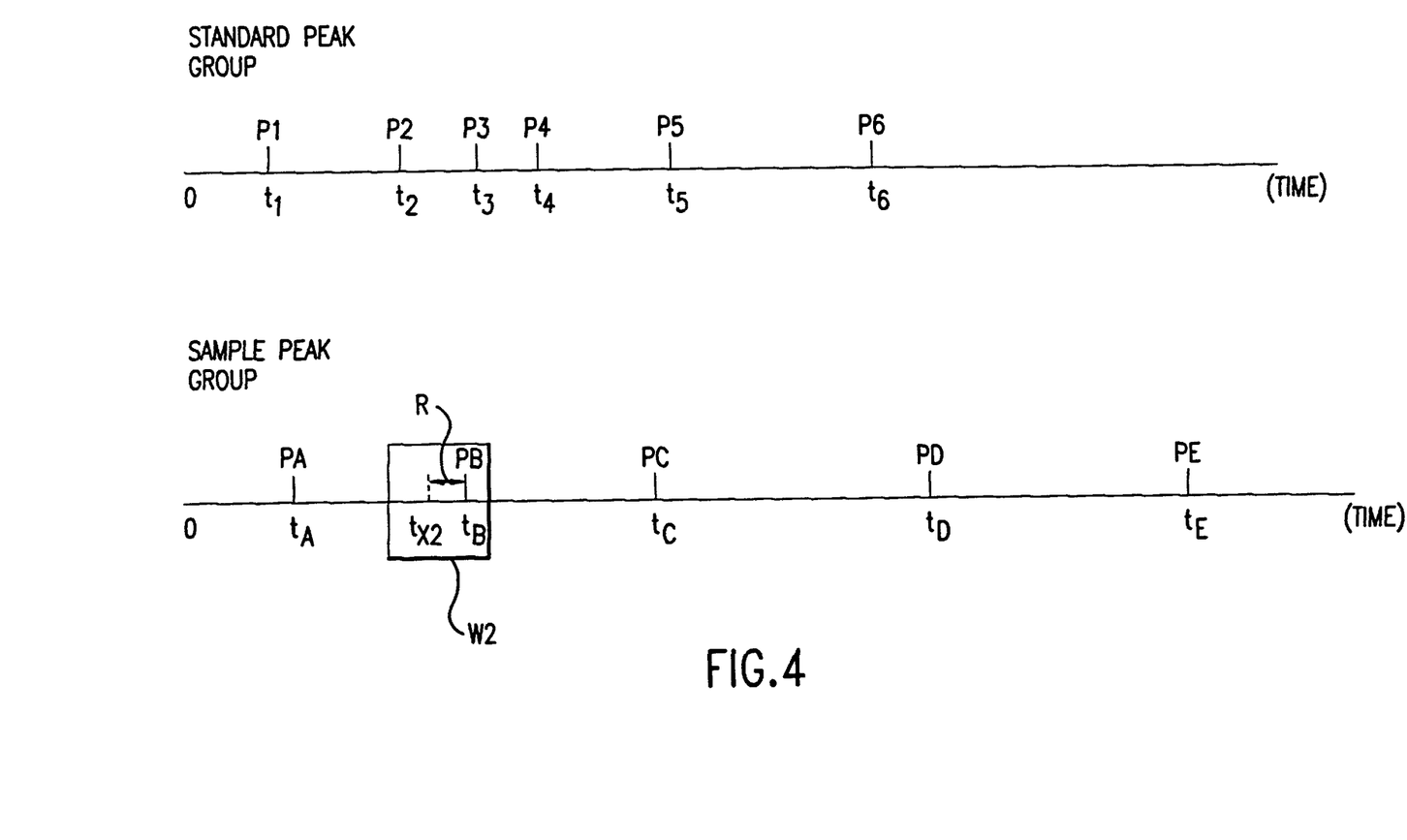
FIG. 4 is a simplified schematic representation of a method step for determining a stretch parameter.

As illustrated in FIG. 4, the preferred method continues in a second step by deriving a second window W2 for matching the next standard peak in the standard peak group with a sample peak. In the illustrated example, a second window W2 is located at an expected retention time $t_{x2}$ derived from the characteristic retention time $t_2$ of the standard peak P2. In the illustrated embodiment, the expected retention time $t_{x2}$ equals the characteristic retention time $t_2$ of the standard peak P2 plus the shift parameter S as determined in the previous step.

The width of the retention time window W2 may be determined from a predetermined or stored value so as to be less than that of W1, or may be determined by a user defined parameter that is preferably chosen by the user to be smaller then the previous retention time window W1.

For each candidate sample peak found within this second retention time window W2, a stretch parameter R is determined. As illustrated in FIG. 4, the second retention time window W2 captures one candidate peak, i.e., sample peak PB that exhibits a respective observed retention time $t_B$ which is used to determine a stretch parameter R from the ratio of: a) the observed retention time $t_B$ for the second sample peak PB minus the observed retention time $t_A$ for the first sample peak PB, and: b) the characteristic retention time of the respective standard peak P2 minus the characteristic retention time $t_1$ of the respective standard peak P1, as follows:

$$R = (t_B - t_A)/(t_2 - t_1)$$

This stretch parameter R is then used in computations to locate the third window W3, fourth window W4, etc.

If there were no sample peaks found within the second window W2, the method would assume that the compound associated with the second standard peak P2 is absent in the sample. The peak identification method would then continue by application of another window to the sample peak series at an expected retention time corresponding to the characteristic retention time of the next standard peak. For example, if the second window W2 failed to capture a sample peak, no sample peak would be considered to be matched with the second standard peak P2 and the next standard peak to be used would be standard peak P3. The peak identification method would then continue by application of a third window W3 to the sample peak series at an expected retention time $t_{x3}$ that equals the characteristic retention time $t_3$ of the standard peak P3 plus the shift parameter S as determined in the previous step. If no sample peak is then captured by the third retention time window, additional windows are created in sequential fashion until at least one sample peak is captured, or until the end of the standard peak group is reached. As illustrated, one sample peak is captured within the second window W2, and it is therefore considered to be matched to the second standard peak P2.

If more than one candidate peak were to be captured in the window W2, the method would proceed in matching subsequent standard peaks with use of a series of stretch parameters (R, R', R" . . . etc.) that are respectively derived from each candidate peak. That is, each candidate peak in the second window W2 results in a stretch parameter that is unique to the respective candidate peak. The method then continues recursively with the remaining peaks in the standard peak group.

Figure 5:
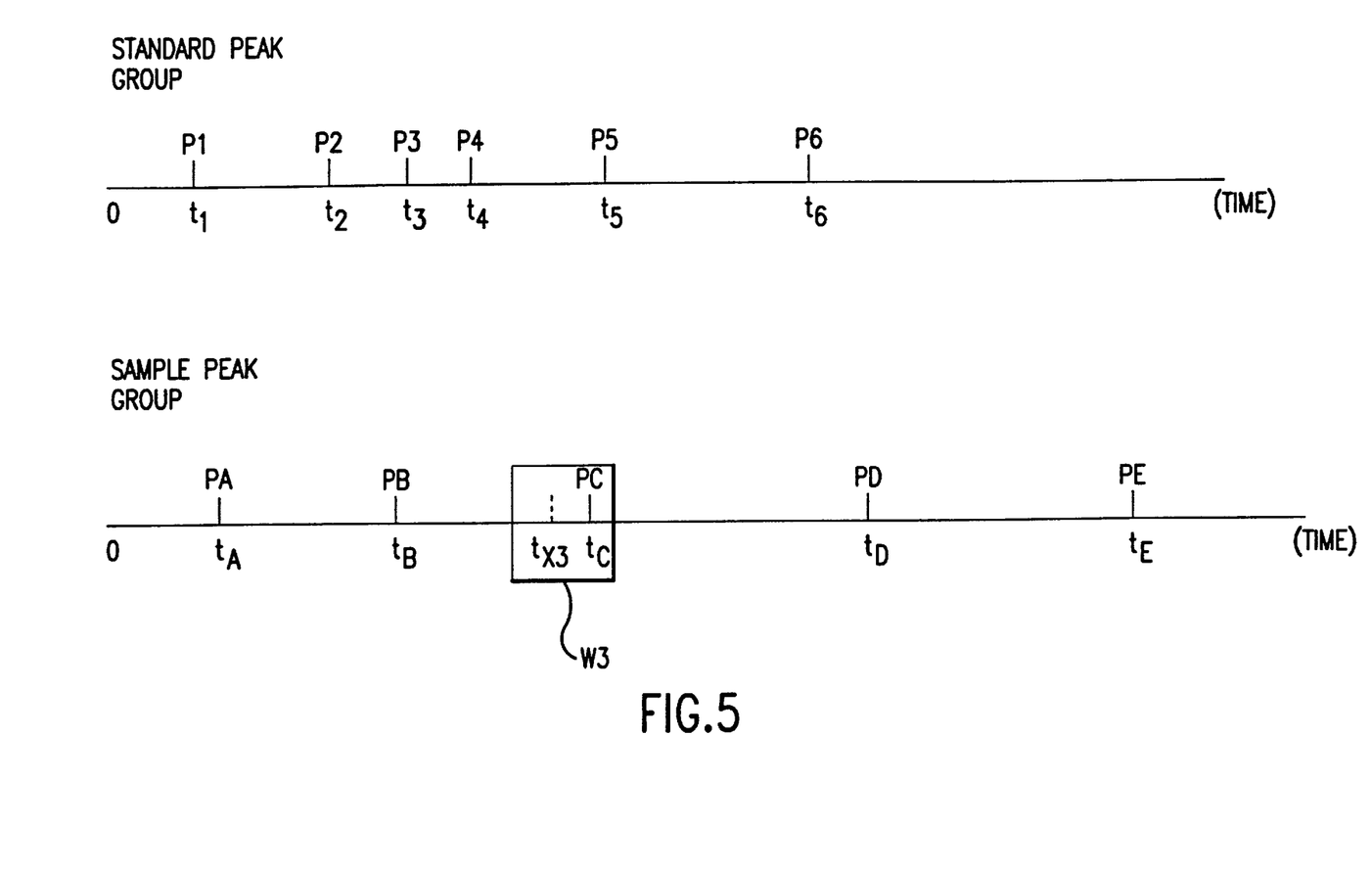
FIG. 5 is a simplified schematic of a method step for determination of a first distort error term.

The method is then continued with respect to the next standard peak to be matched, so as to determine at least one distort parameter. As shown in FIG. 5, a third window W3 is applied to the sample peak series at an expected retention time $t_{x3}$ derived according to the next standard peak P3 at its respective characteristic retention time $t_3$ with, however, an adjustment computed from the shift parameter S and stretch parameter R. The width of the third window W3 is predetermined according to a stored value or set according to a user-defined input parameter, and is expected to accommodate the stochastic movements of the sample components during the separation process. As illustrated in FIG. 5, the third window W3 is centered about an expected retention time $t_{x3}$ that is determined according to the formula:

$$t_{x3} = R(t_3 - t_2) + t_B$$

As shown in FIG. 5, a third sample peak PC is found to occur within the third window W3. In the illustrated embodiment, one sample peak PC is captured. A determination of a distort parameter $D_n$ associated with the respective sample peak PC is then made according to the difference between the expected retention time $t_{x3}$ and the actual retention time $t_C$ of the particular sample peak. The distort parameter will then be used as an error term as will be described below. As illustrated in FIG. 5, as the match of the third standard peak with the sample peak PC is determined, a first distort term $D_1$ is computed according to the formula:

$$D_1 = t_c - t_{X3}$$

If a plurality of sample peaks were to be captured, each sample peak in the third window W3 would be considered a candidate peak, as described hereinabove, for generation of respective distort parameters D, D', D", etc.

Figure 6:
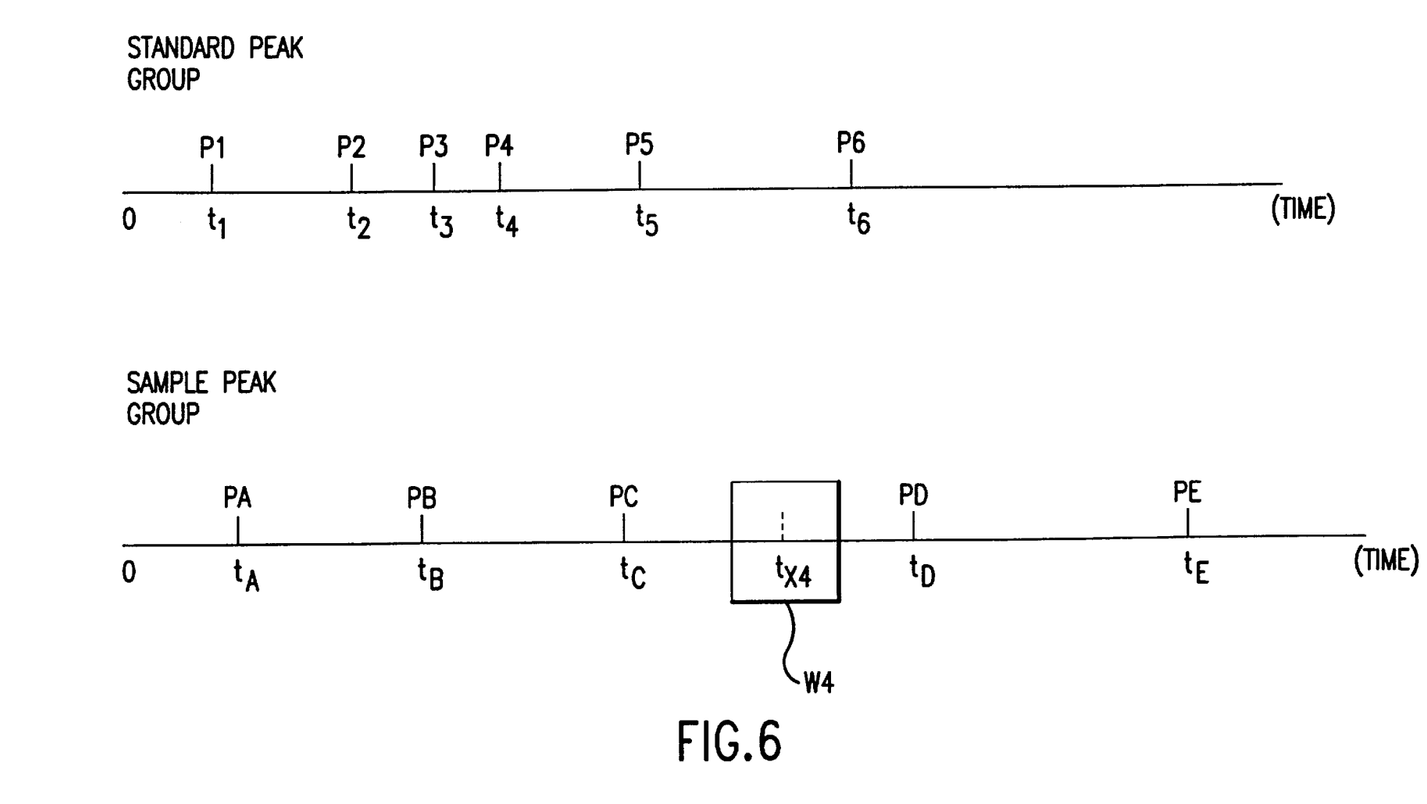
FIGS. 6 & 7 are simplified schematic representations of method steps for the determination of a stretch parameter in the instance of the absence of a particular sample peak in a window created with respect to a known standard peak, wherein the absent peak is skipped and a new window is created using the next peak in the standard peak group.
Figure 7:
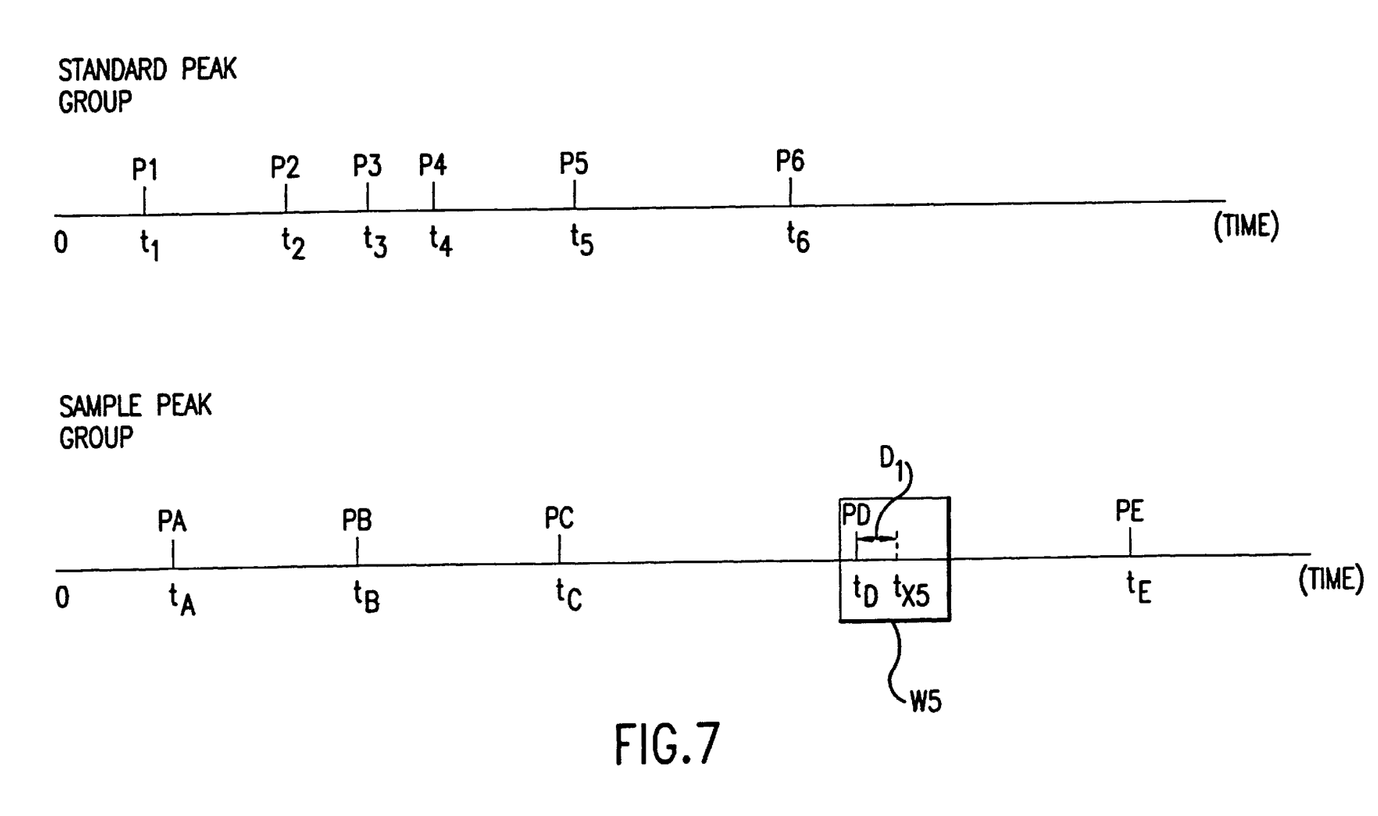

As in previous steps in the process, if the third window W3 does not capture a sample peak, it is assumed that the respective standard peak cannot be matched; the next peak in the standard peak group would be selected for matching. For example, and as illustrated in FIGS. 6 & 7, a fourth window W4 is centered about an expected retention time $t_{X4}$ that is determined according to the formula:

$$t_{X4} = R(t_4 - t_3) + t_c$$

however no candidate peak is found within the fourth window W4 and the particular compound associated with the respective standard peak P4 is assumed to be missing. The standard peak P4 is assumed to be unmatched with any sample peak in the sample peak series. With no candidate peak present, the method continues with use of the previously identified candidate peak (PC) within the sample peak group and its corresponding standard peak (P3). As illustrated in FIG. 7, a fifth window W5 is provided at an expected retention time $t_{X5}$ derived from the characteristic retention time $t_5$ of the fifth standard peak P5 with an adjustment according to the stretch parameter R applied to the difference between the characteristic retention times $t_5$ and $t_3$ of standard peaks P5 and P3, respectively. That is, $$t_{X5} = R(t_5 - t_3) + t_c$$

As illustrated, a distort parameter D, may be observed in the illustrated example because the observed retention time $t_D$ of the fourth sample peak PD does not coincide with the expected retention time $t_{X5}$.

The foregoing step for determination of a distort parameter is then reiterated to calculate similar distort parameters $D_2, D_3 \ldots$ from the respective standard peaks P5, P6, . . . etc.

As a result of the foregoing steps, the preferred method may be found to have generated a plurality of sets of matched pairs wherein each set includes a set of sample peaks that have been matched with some or all of the standard peaks in the standard peak group. If necessary, each pair set is preferably compared with another pair set to determine the quality of the match of each pair set, that is, which pair set exhibits a more accurate match. The best match is then considered to be determinative of which sample peaks are best matched to respective standard peaks, and the sample peaks may then be properly identified.

In the preferred embodiment, two criteria for such quality are: (1) the pair set having a greater number of peaks named, and (2) the pair set that exhibits the minimum total error shown by the error terms for the peaks in the subject pair set. Those skilled in the art will recognize that other criteria can find useful application in a peak identification method according to the present invention.

More particularly, in the preferred embodiment, a figure of merit for the match quality of a set of n matched pairs, termed herein a quality factor Q, may be determined as the sum of the squares of all error terms (i.e., the shift parameter, stretch parameter, and the distort parameter) for all matched peaks in the pair set as follows:

$$Q = \text{Sum of(error term)}^2 = S^2 + R^2 + (D_1)^2 + (D_2)^2 + (D_3)^2 + \ldots (D_n)^2$$

For example, in one preferred embodiment, if the quality determination indicates that a current pair set exhibits a more accurate match, the current pair set may be saved. If the result of a previous match is found to be more accurate then the current match, the results of the current match may be ignored.

Figure 8:
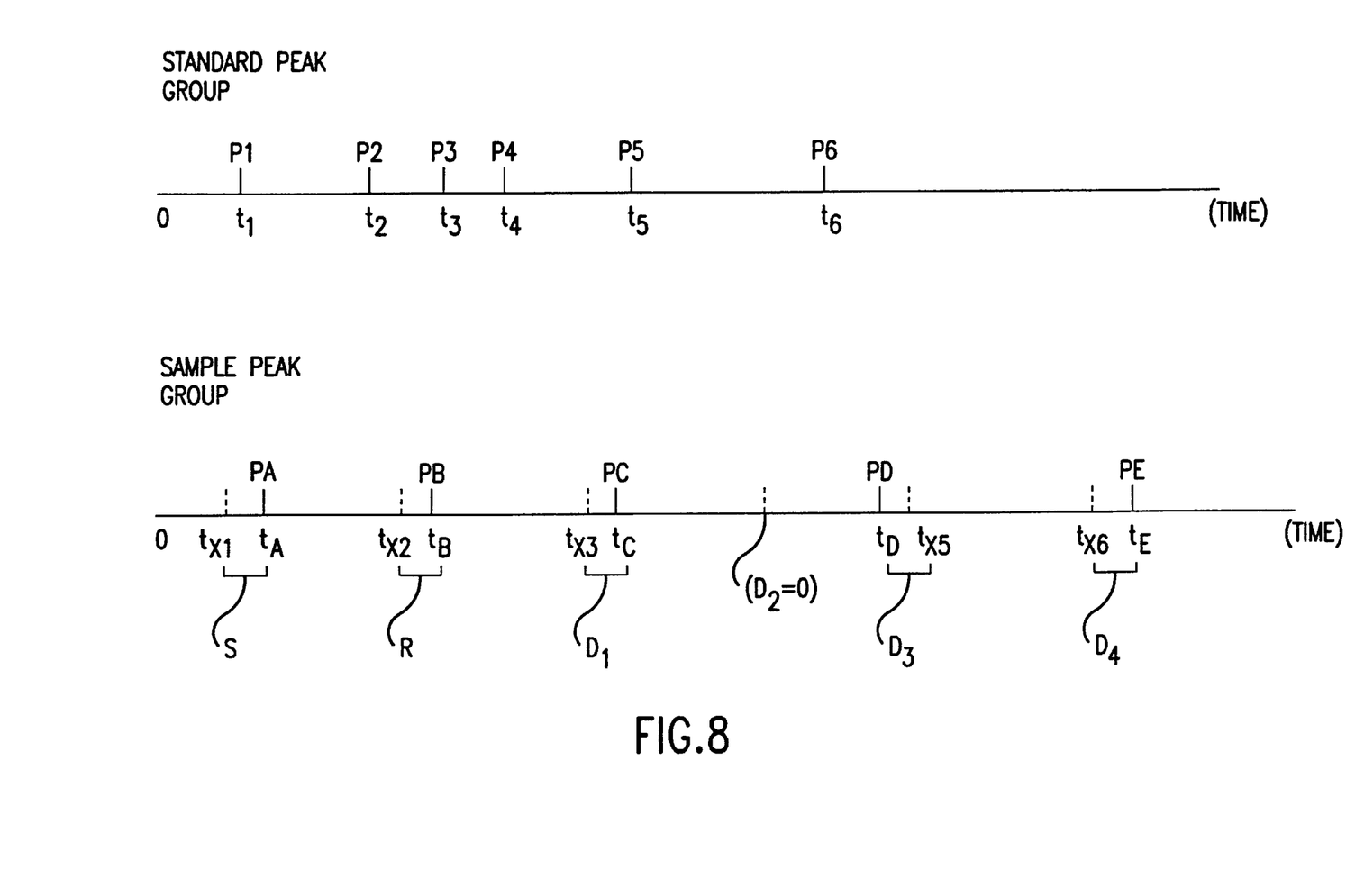
FIG. 8 is a simplified schematic representation of a method step for the determination of a best match condition. In the illustrated embodiment, the best match condition is determined according to the largest number of selected peaks in the sample peak, and secondly according to the minimum sum of the squares of error terms.

As illustrated in FIG. 8, the total error is preferably determined by the sum of the squares of the shift parameter S derived according to the placement of sample peak PA; the stretch parameter R derived according to the placement of the sample peak PB, and the distort terms derived from the observed retention times $t_C$, $t_D$, and $t_E$ of the third, fourth and fifth sample peaks PC, PD, and PE.

Having completed use of the first standard peak group, the method continues by selecting a new standard peak group from the standard peak series and returns to the first steps in the above-described procedure to calculate a new succession of retention time windows using shift, stretch, and distort parameters that are unique to the new standard peak group. It is contemplated that if a retention time window then captures a previously-matched sample peak, the sample peak thus captured is not included for matching as a candidate sample peak.

In an alternative embodiment, when specifying the standard peak group to be applied to a particular sample peak series, a user may specify that certain standard peaks must be matched with at least one sample peak to obtain a valid match. In the subsequent determination for an optimum match, a process step may be included to insure that all required peaks are present. If not, the match may be deemed invalid and thus not used in later steps, such as in a quality factor determination.

What is claimed is:

1. A method for peak identification of a group of sample peaks in a sample peak series present in a chromatogram, with reference to a single standard peak series, comprising the steps of:

determining a succession of first, second, and third retention time windows located according to the characteristic retention times of respective first, second, and third standard peaks selected from a group of standard peaks in the standard peak series; adjusted by shift, stretch, and distort parameters derived from the characteristic retention times of the first, second, and third standard peaks and from the retention times of at least first, second, and third candidate sample peaks respectively captured in the first, second, and third retention time windows;

establishing three or more pairs of selected ones of the first, second, and third standard peaks with selected ones of the first, second, and third candidate sample peaks; and determining the quality of the match of the candidate sample peak with its respective standard peak in said three or more pairs so as to establish a selected candidate sample peak best matched with a respective standard peak;

identifying each sample peak best matched to its respective standard peak in accordance with an identifier associated with the respective standard peak;

whereby the sample peaks in the group of sample peaks are identified.

2. The method of claim 1, wherein the step of best matching the first, second, and third standard peaks with the first, second, and third sample peaks further comprises the step of:

matching a selected one of the first, second, and third standard peaks with a selected one of a plurality of candidate peaks located within at least one of the first, second, and third retention time windows.

3. The method of claim 2, further comprising the steps of:

determining the presence of a plurality of candidate sample peaks in a selected one of the first, second, and third retention time windows with respect to a respectively selected standard peak;

determining a plurality of matched pairs each of which including the selected standard peak;

determining a plurality of quality factors each of which representing the correspondence of the standard peak to a respective one of the candidate sample peaks in the matched pairs;

comparing the plural quality factors to determine a best matched pair of the standard peak and a selected one of the plurality of candidate sample peaks;

identifying the selected candidate sample peak in the best matched pair with a compound associated with the respective selected standard peak.

4. The method of claim 3, further comprising the steps of:

determining, for a set of matched pairs, a resulting string of error terms in an error term series $e_1, e_2, e_3, \ldots e_n$;

summing the squares of the error terms to provide a quality factor; and and wherein the step of best match determination is performed according to the quality factor.

5. The method of claim 1, further comprising the steps of:

selecting first, second, . . . ith standard peaks from a standard peak group;

locating a first retention time window on the chromatogram at a first expected retention time $t_{X1}$ wherein the first expected retention time $t_{X1}$ is determined from a first characteristic retention time $t_1$ associated with the first standard peak;

capturing in the first retention time window at least a first candidate sample peak;

determining the difference between the observed retention time $t_A$ of the first candidate sample peak and the first characteristic retention time $t_1$ and in response providing shift parameter S;

in the event that additional candidate sample peaks are captured in the first retention time window, determining the observed retention time of each candidate sample peak, and in response providing a respective shift parameter S', S", etc.;

locating a second retention time window on the chromatogram at a respective expected retention time $t_{X2}$ wherein the second expected retention time $t_{X2}$ is determined from a second characteristic retention time $t_2$ associated with the second standard peak and wherein the second expected retention time $t_{X2}$ includes a time shift according to the shift parameter S;

capturing in the second retention time window at least a second candidate sample peak;

determining a stretch parameter R according to the ratio of: a) the difference between an observed retention time $t_B$ of the second candidate sample peak and an observed retention time $t_A$ of the first candidate sample peak, and b) the difference between the characteristic retention time $t_2$ of the second standard peak and the characteristic retention time $t_1$ of the first standard peak;

in the event that additional candidate sample peaks are captured in the second retention time window, determining the observed retention time of each candidate sample peak and determining a respective stretch parameter R', R", . . . etc.;

locating a third retention time window on the chromatogram at a respective expected retention time $t_{X3}$ determined from a third characteristic retention time $t_3$ associated with the third standard peak, wherein the expected retention time $t_{X3}$ is provided by the formula:

$$t_{X3}=t_B+R(t_3-t_2)$$

capturing in the third retention time window at least a third candidate sample peak;

determining a distort parameter D according to the difference between the observed retention time $t_C$ of the third candidate sample peak and the expected retention time $t_{X3}$ according to the formula:

$$t_{ei}=t_{(I-1)}+R(t_i-t_{(I-1)}); \text{ and}$$

in the event that additional candidate sample peaks are captured in the third retention time window, determining the observed retention time of each candidate sample peak and determining a respective distort parameter D', D", . . . etc.

6. The method of claim 5, further comprising the steps of:

determining the sample peak to be missing in an instance wherein a retention time window does not capture a candidate sample peak and in response skipping that retention time window and the standard peak with which it is associated;

generating a (I+1)th retention time window in the same fashion as the skipped window but at a next expected retention time $t_{X(n+1)}$; and wherein the corresponding sample peak thus captured is associated with the (I+1)th, standard peak;

whereby a series of sample peaks may be identified even though the number of sample peaks present in the sample peak group differs from the number of peaks in the standard peak group.

7. The method of claim 4, further comprising the steps of:

determining a width for a selected one of the first, second, and third retention time windows, wherein the width for the selected retention time window is less than that of a previous retention time window.

8. The method of claim 4, wherein at least one quality factor is determined according to a first criterion associated with the number of captured candidate sample the peaks in a matched peak set, and a second criterion associated with the minimum sum of the squares of the error terms in the error term series devoted to the matched peak set, and further comprising the step of comparing the quality factors to determine the best match of a respective selected peak set to the standard peak group.

9. The method of claim 1, wherein the standard peak series comprises plural groups of standard peaks, wherein the standard peak groups have been generated by respectively differing columns operated in a multidimensional chromatographic analysis.

10. The method of claim 1, further comprising the steps of providing a peak in a standard peak group with a component name, a characteristic retention time, a group identifier and using at least one of the component name, characteristic retention time, and group identifier in the identification of a sample peak.

11. A method for peak identification of a group of sample peaks in a sample peak series present in a chromatogram, with reference to at least one group of standard peaks in a single standard peak series, comprising the steps of:

I. selecting a first standard peak from the group of standard peaks;

II. applying a first retention time window corresponding to a first standard peak retention time to the sample peak series to capture a first set of one or more first candidate sample peaks for matching to the first standard peak;

III. selecting, in succession, each of the first candidate sample peaks and calculating a respective shift value (S, S', S" . . .) according to the difference between the retention time of the first standard peak and the retention time of a selected one of the first candidate sample peaks, and with respect to each of the first candidate sample peaks:

(A) selecting a second standard peak, (B) locating a second retention time window at a time calculated according to the retention time of the second standard peak adjusted by a selected one of the shift values (S, S', S" . . .) and applying the second retention time window to the sample peak series to capture a second set of candidate sample peaks containing one or more second candidate sample peaks for matching to the second standard peak;

(C) selecting, in succession, each of the second candidate sample peaks in the second set of candidate sample peaks and calculating a respective stretch parameter (R, R', R" . . .) based on the time difference between the retention time of the second standard peak and the selected second candidate sample peak, and with respect to each of the second candidate sample peaks:

(1) selecting a third standard peak;

(2) locating a third retention time windows at a time calculated according to the retention time of the third standard peak time and adjusted by a distort value ($D_1, D_2, D_3$ . . .) calculated according to the shift values (S, S', S" . . .) and the stretch values (R, R', R" . . .), so as to capture a respective third set of candidate sample peaks, the third set containing third candidate sample peaks for matching to the third standard peak;

(3) determining, for selected ones of the candidate sample peaks in the first, second, and third sets of candidate sample peaks, a plurality of pairs of selected candidate sample peaks with a respective one of the first, second, and third standard peaks;

(4) recursively continuing the above steps(1)–(3) for a plurality of candidate sample peaks within the third retention time window;

(D) recursively continuing the above steps (A)–(C) for a plurality of candidate sample peaks within the second retention time window;

IV. recursively continuing the above steps I–III for a plurality of candidate sample peaks within the first retention time window;

V. identifying selected ones of the sample peaks in the sample chromatogram by determining which of the selected sample peaks and the corresponding standard peaks provide a best match quality factor.

12. The method of claim 11, wherein a selected one of steps IV–VI further comprise the step of, in the event that no candidate sample peak is captured in one of the series of the first retention time windows, selecting a succeeding standard peak as the first standard peak, and in the event that no candidate sample peak is captured in one of the series of the second retention time windows, selecting a succeeding standard peak as the second standard peak.

13. The method of claim 11, further comprising the steps of:

calculating a respective error term based on the difference between the retention time of a particular one of the first, second, and third standard peaks and the respective candidate sample peak;

wherein the step of calculating the error term further comprises the steps of: (a) recursively selecting the $n^{th}$ standard peak in a group of n standard peaks, determining a match with the candidate sample peak, and calculating an error term; and (b) calculating a match quality factor based on the sum squared of the error terms, and based on the magnitude of the shift value, stretch value, and the number of matched peaks.

* * * * *

UNITED STATES PATENT AND TRADEMARK OFFICE
CERTIFICATE OF CORRECTION

PATENT NO. : 5,905,192
DATED : May 18, 1999
INVENTOR(S) : Edwin E. Wikfors; Charles N. Carter It is certified that error appears in the above-indentified patent and that said Letters Patent is hereby corrected as shown below:

Claim 7, line 1, "claim 4" should read -- claim 1 -- .

Signed and Sealed this

Twenty-eighth Day of December, 1999

*Attest:*

Q. TODD DICKINSON

*Attesting Officer*   *Acting Commissioner of Patents and Trademarks*